(12) United States Patent
Steinmann (10) Patent No.: US 7,452,381 B2
(45) Date of Patent: Nov. 18, 2008

(54) RADIAL HEAD REPLACEMENT SYSTEM

(75) Inventor: Scott P. Steinmann, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 413 days.

(21) Appl. No.: 10/767,642

(22) Filed: Jan. 29, 2004

(65) Prior Publication Data

US 2004/0186580 A1    Sep. 23, 2004

Related U.S. Application Data

(60) Provisional application No. 60/443,697, filed on Jan. 30, 2003.

(51) Int. Cl.
*A61F 2/38* (2006.01)
(52) U.S. Cl. .................... 623/23.47; 623/20.11
(58) Field of Classification Search ... 623/18.11–23.42, 623/23.47, 23.43, 1–21.19
See application file for complete search history.

(56) References Cited

U.S. PATENT DOCUMENTS

| | | | |
|---|---|---|---|
| 4,302,855 A | 12/1981 | Swanson | |
| 4,686,978 A | 8/1987 | Wadsworth | |
| 4,718,414 A | 1/1988 | Saunders et al. | |
| 4,736,737 A | 4/1988 | Fargie et al. | |
| 4,927,422 A | 5/1990 | Engelhardt | |
| 5,030,237 A | 7/1991 | Sorbie et al. | |
| 5,108,396 A | 4/1992 | Lackey et al. | |
| 5,522,902 A | 6/1996 | Yuan et al. | |
| 5,534,032 A | 7/1996 | Hodorek | |
| 5,601,565 A | 2/1997 | Huebner | |
| 5,702,457 A * | 12/1997 | Walch et al. ............. | 623/19.13 |
| 5,704,941 A | 1/1998 | Jacober et al. | |
| 5,779,709 A | 7/1998 | Harris, Jr. et al. | |
| 5,782,922 A | 7/1998 | Vandewalle | |
| 5,879,395 A | 3/1999 | Tornier et al. | |
| 6,203,575 B1 * | 3/2001 | Farey ....................... | 623/18.11 |
| 6,206,925 B1 * | 3/2001 | Tornier .................... | 623/19.12 |
| 6,217,616 B1 | 4/2001 | Ogilvie | |
| 6,245,110 B1 | 6/2001 | Grundei et al. | |
| 6,270,529 B1 | 8/2001 | Terrill-Grisoni et al. | |
| 6,361,563 B2 | 3/2002 | Terrill-Grisoni et al. | |
| 6,428,577 B1 * | 8/2002 | Evans et al. .............. | 623/20.29 |
| 6,589,282 B2 * | 7/2003 | Pearl ........................ | 623/19.14 |
| 6,620,199 B2 | 9/2003 | Greisamer | |
| 6,656,225 B2 | 12/2003 | Martin | |

(Continued)

*Primary Examiner*—Corrine McDermott
*Assistant Examiner*—Cheryl Miller
(74) *Attorney, Agent, or Firm*—Quarles & Brady, LLP (57) ABSTRACT

A radial head replacement system includes a radial head replacement, an apparatus for guiding the resection of a radial head, and a kit including bone plug and bone plug insertion instrument. The radial head replacement has a separate adjustable head portion that may be secured on an implanted stem such that the implanted radial head replacement smoothly interfaces with the capitellum of the humerus. In another form, the radial head replacement uses crossed bone screws that serve to more securely anchor the stem of the radial head replacement in the intramedullary canal of the radius. The resection guide includes a movable cutting guide which ensures a precise resection of the radial head and thereby allows for better positioning of the implanted radial head replacement. The bone plug limits the travel of bone cement beyond the area of affixation of the stem portion of a radial head replacement to the radius.

16 Claims, 11 Drawing Sheets

U.S. PATENT DOCUMENTS

| | | | |
|---|---|---|---|
| 6,821,300 B2 * | 11/2004 | Masini | 623/23.2 |
| 6,887,277 B2 * | 5/2005 | Rauscher et al. | 623/19.13 |
| 6,986,790 B2 * | 1/2006 | Ball et al. | 623/19.11 |
| 2001/0037154 A1 | 11/2001 | Martin | |
| 2002/0055744 A1 * | 5/2002 | Reiley | 606/79 |
| 2002/0120339 A1 * | 8/2002 | Callaway et al. | 623/19.14 |
| 2003/0114859 A1 | 6/2003 | Grusin et al. | |
| 2003/0158558 A1 | 8/2003 | Horn | |
| 2003/0212457 A1 | 11/2003 | Martin | |

\* cited by examiner

RADIAL HEAD REPLACEMENT SYSTEM

CROSS-REFERENCES TO RELATED APPLICATIONS

This application claims priority from U.S. Provisional Patent Application No. 60/443,697 filed Jan. 30, 2003.

STATEMENT REGARDING FEDERALLY SPONSORED RESEARCH

Not Applicable.

BACKGROUND OF THE INVENTION

1. Field of the Invention

This invention relates to an elbow prosthesis, and more particularly to a replacement for the radial head and to methods and instruments for use in replacing a radial head.

2. Description of the Related Art

Fractures of the radial head constitute one of the most common fractures of the elbow. Radial head fractures can be treated by excision of the head of the radius. However, this can lead to joint pain and elbow instability. As a result, prosthetic radial head replacements have been frequently recommended to obviate the problems associated with excision of the radial head and to improve stability of the elbow joint. Examples of a radial head prosthesis are shown in U.S. Patent Application Publication Nos. 2003/0212457 and 2001/0037154, and in U.S. Pat. Nos. 6,656,225, 6,361,563, 6,270,529 and 6,217,616.

Radial head replacements generally include a stem portion designed to extend into the intramedullary canal of the radius and a head portion designed to replace the radial head. When replacing the radial head with a radial head replacement, the radial head is surgically removed and the top of the radius and the intramedullary canal of the radius are prepared for receipt of the stem. A cement material is typically inserted into the open intramedullary canal and the stem is driven into the canal. Often, the stem is fixed to the radius with a curable acrylic polymer cement such as polymethylmethacrylate. Alternatively, the stem may be fixed to the radius using an interference fit (i.e., "press fit") without cement. In another alternative, the radial head replacement may be fixed to the radius using bone screws.

While existing radial head replacements provide satisfactory results for most purposes, they do have drawbacks. For example, it may be difficult to position known radial head replacements such that the end surface of the head portion of the implanted radial head replacement smoothly interfaces with the capitellum of the humerus. In extreme cases, the implanted radial head replacement may even dislocate such that intefacial contact with the capitellum is precluded.

One source of this positioning problem is the lack of adjustability of known radial head replacements. Existing radial head replacements are typically unitary in design and therefore, do not allow for relative movement between the stem portion and the head portion. Thus, the position of the head portion cannot be adjusted in relation to the stem portion after the stem portion is inserted in the intramedullary canal of the radius.

Another source of this positioning problem is the inaccuracy of some osteotomy cuts of the natural radial head. Generally, the osteotomy cut of the natural radial head must be made so that the angle of the cut corresponds to the angle between the stem and head portions of the radial head replacement. Inaccurate resection can result in an ill-fitting radial head replacement which may lead to the dislocation risks noted above. Various resection guides have been proposed in the orthopedic field. See, for example, U.S. Pat. Nos. 5,779,709, 5,704,941, 5,601,565, 5,108,396, 4,927,422, 4,736,737, 4,718,414, and 4,686,978 and U.S. Patent Application Publication Nos. 2003/0158558 and 2003/0114859.

Another problem with radial head replacement procedures may develop from the employment of a bone cement for fixation of the stem to the radius. This problem is primarily related to limitation of the cement to the area of the stem within the intramedullary canal of the radius. Specifically, the cement may travel beyond the area of affixation in the radius. Proper fixation of the stem to the radius may not be achieved without taking steps to limit the travel of the cement. U.S. Pat. No. 4,302,855 has proposed one solution to this problem.

Yet another problem with radial head replacement procedures may develop from the use of bone screws for fixation of the radial head replacement to the radius. For example, bone screws may not provide for optimum fixation of the radial head replacement to the radius.

Thus, there is a need for an improved radial head replacement that provides for better contact with the capitellum of the humerus. In particular, there is a need for a radial head replacement that can be adjusted so that the head portion of the implanted radial head replacement smoothly interfaces with the capitellum of the humerus. There is also a need for a radial head replacement that provides for improved fixation of the radial head replacement to the radius. There is also a particular need for a radial cutting guide which ensures a precise resection of the radial head and thereby allows for better positioning of the implanted radial head replacement. There is also a need for a means for limiting the travel of bone cement beyond the area of affixation of the stem portion of a radial head replacement to the radius.

SUMMARY OF THE INVENTION

The foregoing needs are met by a radial head replacement system according to the invention. The radial head replacement system may include a prosthesis for replacing the radial head, an apparatus for guiding the resection of the radial head, and a kit for plugging an open end of the intramedullary canal of the radius to restrict the flow of a cement used to fix the prosthesis stem.

In one aspect, the invention provides a modular prosthesis for replacing a radial head. The modular prosthesis has a stem dimensioned to be received in the intramedullary canal of the radius, and a head having an outer wall defining an interior space dimensioned such that the head can be placed over an end portion of the stem. The outer wall of the head is dimensioned such that the head can be moved: (i) in an axial direction in relation to an axis of the stem, and/or (ii) in a first transverse direction in relation to the axis of the stem, and/or (ii) in a second transverse direction at an angle to the first transverse direction when the head is placed over the end portion of the stem.

The modular prosthesis includes at least one opening in the outer wall of the head and a screw dimensioned to be arranged in each opening. Each screw is suitable for contacting the end portion of the stem when arranged in its associated opening to secure the head to the stem by constraining movement of the head in the axial direction and/or in the transverse directions.

The separate head, stem, and screw(s) of the modular prosthesis provide a radial head replacement system wherein the head portion of the implanted radial head replacement can be positioned in any number of spatial relationships relative to the stem and thereafter secured to the stem such that the head smoothly interfaces with the capitellum of the humerus and the radial notch of the ulna. The head may be adjustable in three planes: lateral-medial (a transverse direction in relation to the axis of the stem), posterior-anterior (another transverse direction in relation to the axis of the stem), and proximal-distal (an axial direction in relation to the axis of the stem) before being secured to the stem. As a result, the risk that the implanted radial head replacement may dislocate is minimized. Thus, the modular prosthesis overcomes the difficulties in getting the radial head replacement to track over the capitellum of the humerus.

In another aspect, the invention provides a prosthesis having a head, a stem extending away from the head, and at least two screws. The stem is dimensioned to be received in the intramedullary canal of the radius. The prosthesis includes a first channel extending diagonally from a first side of the head to an opposite second side of the stem. The prosthesis also includes a second channel extending diagonally from a second side of the head to an opposite first side of the stem. A screw is associated with and arranged in each channel such that the prosthesis can be secured to the bone by driving each screw arranged in each channel into the radius. The crossed bone screws serve to more securely anchor the stem of the radial head replacement in the intramedullary canal of the radius without the need for cement.

In yet another aspect, the invention provides an apparatus for guiding the resection of the radial head. The apparatus includes an intramedullary alignment shaft dimensioned to be received in the intramedullary canal of the radius, and a movable cutting guide suitable for placing on the shaft. The cutting guide has a base for placing on the shaft and a wall extending laterally away from the base in a direction of the shaft axis. The wall terminates in an outermost cutting guide edge for guiding the resection of the end of the bone. The surgeon may move the cutting guide to a desired location over the radius and then the radius is resected accurately using a conventional surgical saw guided by the outermost cutting guide edge. As a result, the osteotomy cut of the natural radial head is made at an angle that corresponds to the angle between the stem and head portions of the radial head replacement. Thus, inaccurate resection and the associated dislocation risks noted above are avoided. In another form, the end portion of the alignment shaft includes a cutting guide mounting section that is transversely offset from the alignment shaft to allow the alignment shaft to be placed along the outside of the radius. In either form of the alignment shaft, the alignment shaft may be connected to a concave bearing surface dimensioned to conform to the shape of the capitellum. This also improves the accuracy of the osteotomy cut.

In still another aspect, the invention provides a kit for plugging an open end of the intramedullary canal of the radius to restrict the flow of a cement used to fix the prosthesis stem inserted into the canal. The kit includes a plug of medical grade material and an insertion instrument. The plug is dimensioned to seal the intramedullary canal at a location below an end of the prosthesis stem and prevent flow of cement beyond the location. The insertion instrument is used for placing the plug in the intramedullary canal. The insertion instrument is dimensioned to be received in the intramedullary canal of the bone, and the insertion instrument has a lateral crosspiece to facilitate placement of the plug at a predetermined depth in the intramedullary canal.

Therefore, it is an advantage of the present invention to provide a radial head replacement with an adjustable head portion such that the head portion can be positioned to smoothly interface with the capitellum of the humerus.

It is another advantage of the present invention to provide a radial head replacement that provides for improved fixation of the radial head replacement to the radius by way of diagonally aligned bone screws.

It is still another advantage of the present invention to provide an apparatus with a cutting guide system that ensures a precise resection of the radial head and thereby allows for better positioning of an implanted radial head replacement.

It is yet another advantage of the present invention to provide a means for limiting the travel of bone cement beyond the area of affixation of the stem portion of a radial head replacement to the radius.

These and other features, aspects, and advantages of the present invention will become better understood upon consideration of the following detailed description, drawings, and appended claims.

BRIEF DESCRIPTION OF THE DRAWINGS

Like reference numerals will be used to refer to like or similar parts from Figure to Figure in the following description.

DETAILED DESCRIPTION OF THE INVENTION

The present invention is directed to a radial head replacement system that includes a radial head replacement, an apparatus for guiding the resection of a radial head, and a bone plug and bone plug insertion instrument.

Figure 1:
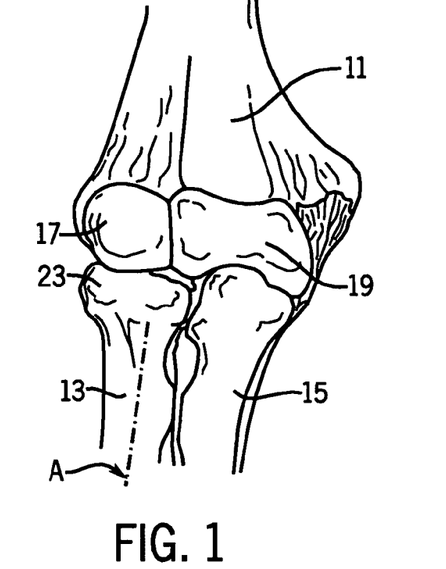
FIG. 1 is a fragmentary view showing the three bones of the human elbow.

In order to provide background for the present invention, portions of U.S. Pat. No. 6,217,616 are included herein. U.S. Pat. No. 6,217,616 describes the functioning of the elbow joint and shows an example prosthesis for replacing the end portion of the radius. Turning to FIGS. 1-7 of the present application, there is shown an elbow joint and the prior art prosthesis of U.S. Pat. No. 6,217,616. Illustrated in FIG. 1 is the distal end portion of the humerus 11 along with the proximal end portions of the radius 13 and the ulna 15. The distal end portion of the humerus includes a portion referred to as the capitellum 17 against which the radius 13 articulates, and a portion referred to as the trochlea 19 against which the ulna 15 articulates. The radius 13 is located on the thumb side of the forearm. The ulna 15 forms a hinge joint with the humerus 11 which allows for flexion and extension of the forearm. The capitellum 17 is located on the lateral side of the humerus 11 and has a convex, generally spherical shape. The ulna 15 includes a trochlear notch 21 which extends in a proximal direction and resides on the posterior of the distal end of the humerus 11. A head 23 of the radius 13 contacts the capitellum 17 of the humerus 11 and a radial notch 25 which is formed in the medial portion of the ulna 15.

Figure 2:
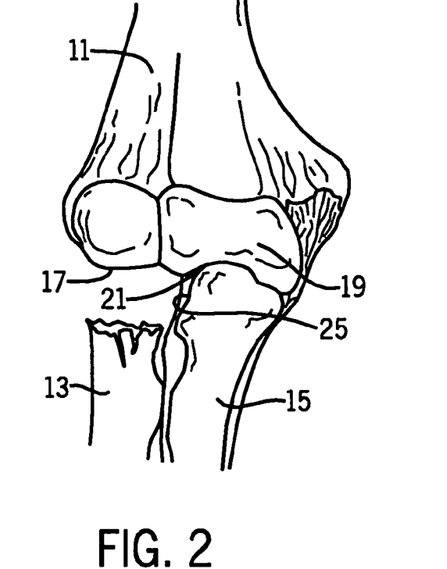
FIG. 2 is a view similar to FIG. 1 where the head of the radius has fractured and been removed.
Figure 3:
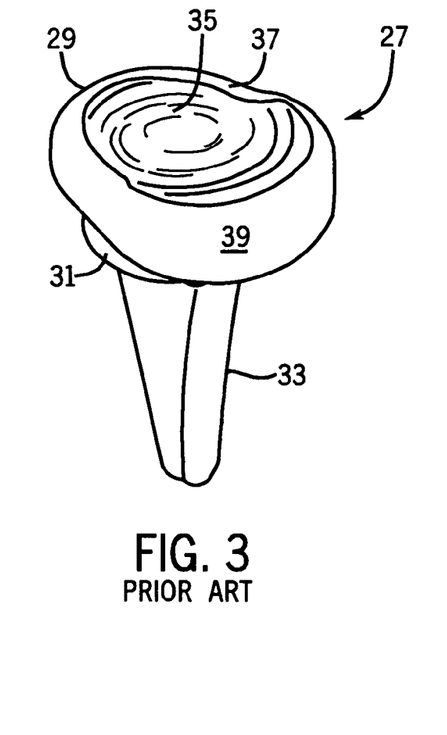
FIG. 3 is a perspective view of the radial head replacement described in U.S. Pat. No. 6,217,616.
Figure 4:
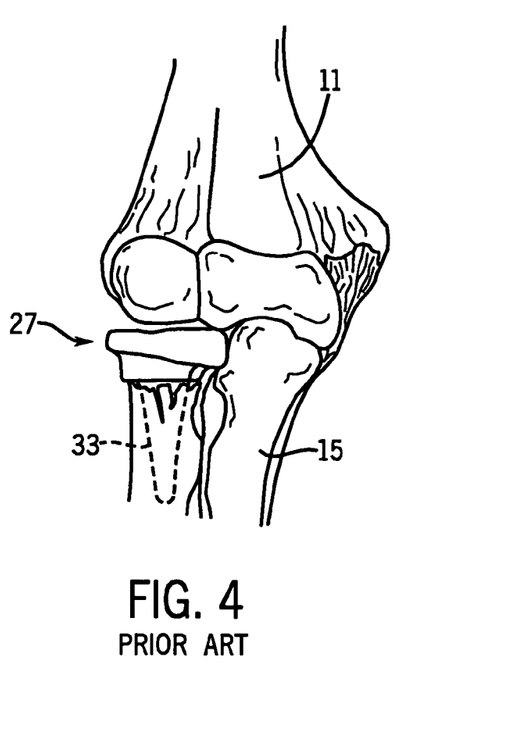
FIG. 4 is a fragmentary view of an elbow, similar to FIG. 2, showing the excised radius having been replaced with the radial head replacement shown in FIG. 3, with spacing provided for clarity of explanation.
Figure 5:
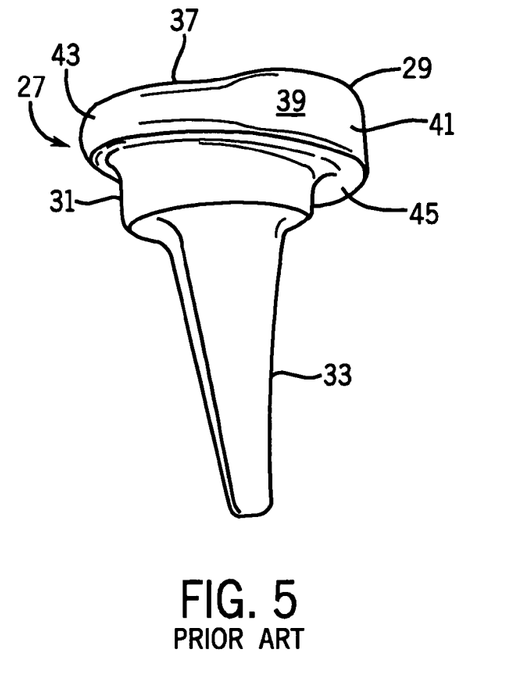
FIG. 5 is a perspective view of the radial head replacement shown in FIG. 3, taken from a different angle.
Figure 6:
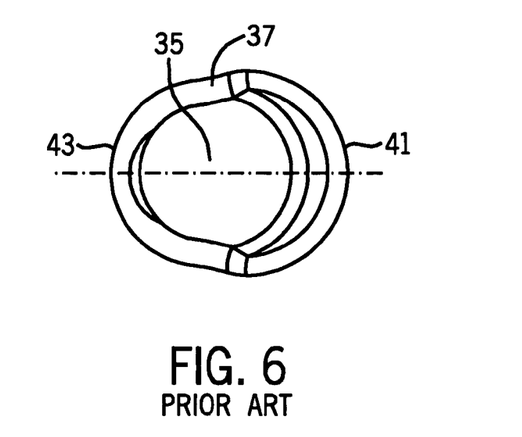
FIG. 6 is a top view of the radial head replacement shown in FIG. 3.
Figure 7:
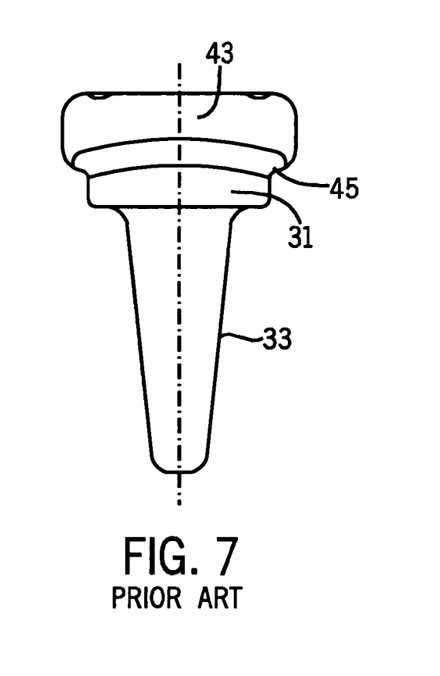
FIG. 7 is a left side elevation view of the radial head replacement shown in FIG. 3.
Figure 8:
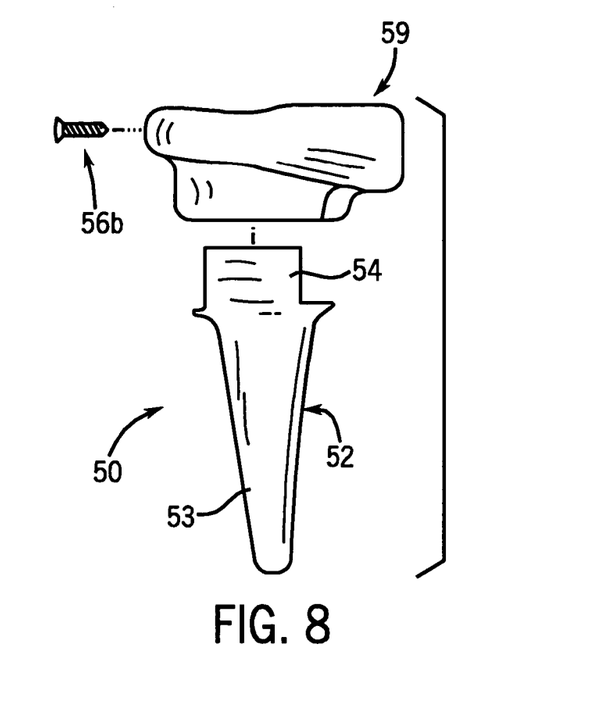
FIG. 8 is a side exploded view of an embodiment of a radial head replacement according to the invention.
Figure 9:
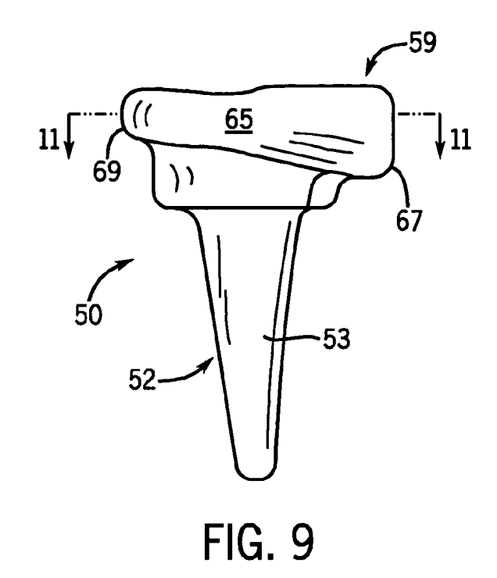
FIG. 9 is a side view of the radial head replacement of FIG. 8 in an assembled condition.
Figure 10:
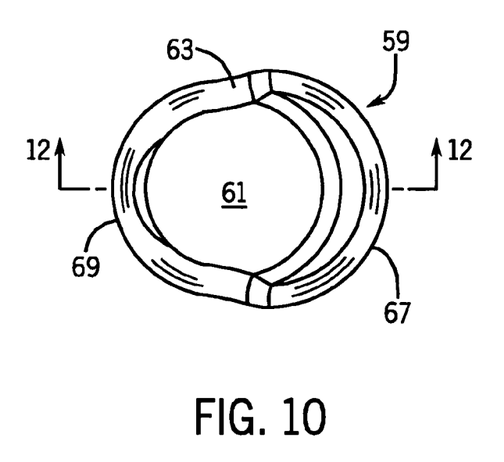
FIG. 10 is a top view of the radial head replacement of FIG. 9.

When it is necessary to replace the proximal head 23 of the radius 13 for any reason, a prosthesis 27 such as that illustrated in FIGS. 3-7 (and described in U.S. Pat. No. 6,217,616) may be used to replace it. FIG. 2 shows an elbow joint with the head of the radius 13 excised, and FIG. 4 shows that joint wherein the head of the radius 13 has been replaced with the prosthesis 27. Looking at FIGS. 4-7, the example known prosthesis 27 (further described in U.S. Pat. No. 6,217,616) has a head 29, a collar 31 and a stem 33, with the stem 33 of the prosthesis being proportioned to be received with the intramedullary cavity of the radius 13. The head portion 29 of the prosthesis has a proximal concave surface 35 which is shaped for contact with the capitellum 17. The radius of curvature of the generally spherical concave surface 35 is matched so as to approximate the radius of curvature of the capitellum 17. This concave surface 35 is surrounded by a peripheral rim 37, which lies at the proximal end of a peripheral surface 39 of the head, which surface extends completely therearound and varies in height as a result of the shape of the head. The head 29 has a medial region 41 and a lateral region 43. The surface of the medial region 41 of the periphery of the head 29 articulates with the depression in the side of the ulna 15 referred to as the radial notch 25. The head 29 also has an undersurface 45 that is substantially planar.

Turning now to FIGS. 8-12, there is shown an embodiment of a radial head replacement 50 according to the invention. The modular radial head replacement 50 includes a head 59, a stem 52 and set screws 56a, 56b, 56c. The stem 52 has a body section 53 and an end portion in the form of a circular plateau 54 that extends upwardly from the top of the body section 53. The body section 53 of the stem 52 is dimensioned to be received within the intramedullary canal of the radius 13.

The head 59 of the radial head replacement 50 has a proximal concave surface 61 which is shaped for contact with the capitellum 17. The radius of curvature of the concave surface 61 is matched so as to approximate the radius of curvature of the capitellum 17. This concave surface 61 is surrounded by a peripheral rim 63, which lies at the proximal end of a peripheral surface 65 of the head 59. The head 59 has a medial region 67 and a lateral region 69. The surface of the medial region 67 of the periphery surface 65 of the head 59 articulates with the radial notch 25 in the side of the ulna 15. The head 59 has an outer wall 71 which forms the concave surface 61, the peripheral rim 63, and the peripheral surface 65 of the head 59. The outer wall 71 of the head 59 defines an interior space 73 of the head 59 (see FIG. 12). The outer wall 71 of the head 59 also includes openings 57a, 57b and 57c that accept the set screws 56a, 56b, 56c, opening 57a being omitted from FIGS. 8 and 9 for clarity. The elliptical design of the head 59 of the radial head replacement 50 better models the normal anatomy of the radial head.

The head 59, the stem 52, and the set screws 56a, 56b, 56c of the radial head replacement 50 are typically provided as separate components for assembly. However, the set screws 56a, 56b, 56c may be provided in a partially inserted state in the head 59. The head 59, the set screws 56a, 56b, 56c, and the stem 52 of the radial head replacement 50 may formed from a biocompatible material such as a titanium alloy (e.g., titanium-6-aluminum-4-vanadium), a cobalt alloy, a stainless steel alloy, a tantalum alloy, a nonresorbable ceramic such as aluminum oxide or zirconia, a nonresorbable polymeric material such as polyethylene, or a nonresorbable composite material such as a carbon fiber-reinforced polymer. Forming the head 59 and the stem 52 of the radial head replacement 50 from a polished cobalt-chromium alloy may be particularly advantageous.

The radial head replacement 50 may be implanted in the radius 13 as follows. First, the head of the radius 13 is resected and the intramedullary canal of the radius 13 is inspected and tools (such as a reamer) may be used to clean material out of the intramedullary canal. Once the intramedullary canal in the radius 13 has been prepared, the surgeon can then "press-fit" the stem 52 (which is tapered for ease of insertion) into the intramedullary canal of the radius 13. Optionally, the stem 52 can be cemented in the intramedullary canal, and/or bone screws can be used to further secure the stem 52 in the intramedullary canal of the radius 13.

Figure 11:
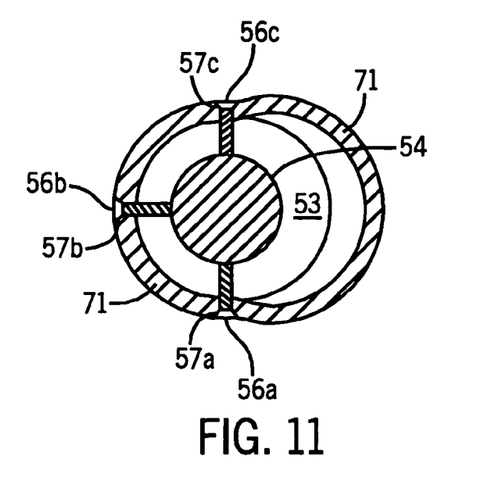
FIG. 11 is a cross-sectional view of the radial head replacement of FIG. 9 taken along line 11-11 of FIG. 9.
Figure 12:
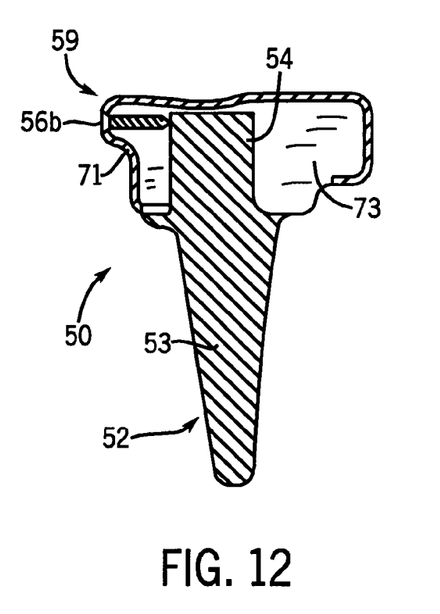
FIG. 12 is a cross-sectional view of the radial head replacement of FIG. 10 taken along line 12-12 of FIG. 10.
Figure 13:
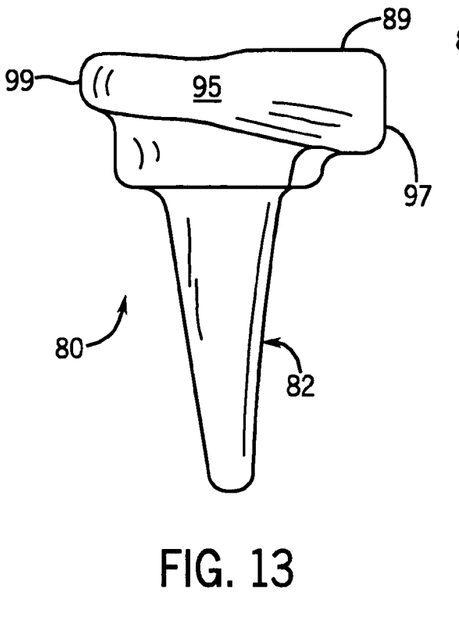
FIG. 13 is a side view of another embodiment of a radial head replacement according to the invention.
Figure 14:
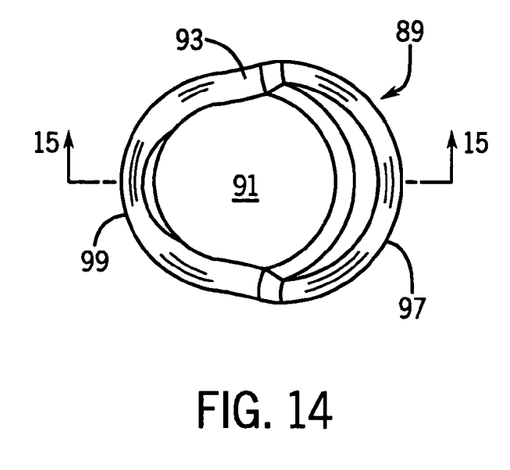
FIG. 14 is a top view of the radial head replacement of FIG. 13.
Figure 15:
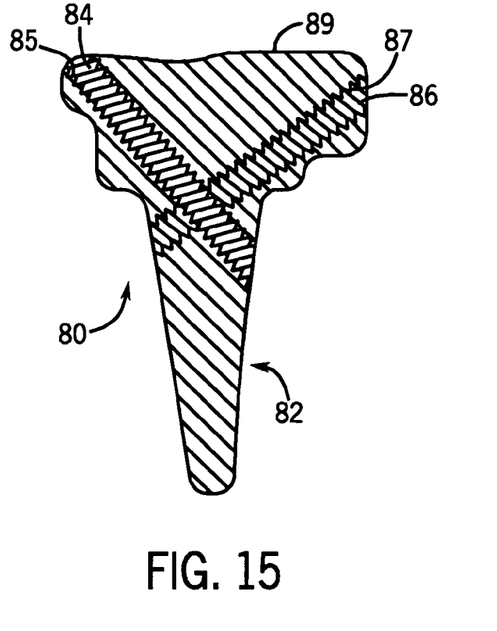
FIG. 15 is a cross sectional view of the radial head replacement of FIG. 14 taken along line 15-15 of FIG. 14.

Next, the head 59 of the radial head replacement 50 is positioned over the stem 52 such that the circular plateau 54 of the stem 52 is within the interior space 73 of the head 59 (see FIG. 12). The head 59 of the radial head replacement 50 is then moved into contact with the ulna 15 and the capitellum 17 such that the concave surface 61 of the head 59 contacts the capitellum 17 of the humerus 11 and the surface of the medial region 67 of the periphery surface 65 of the head 59 contacts the radial notch 25 in the side of the ulna 15. The head 59 of the radial head replacement 50 is held in this position and set screws 56a, 56b, 56c are screwed inwardly until the set screws 56a, 56b, 56c contact the circular plateau 54 of the stem 52 as shown in FIGS. 11 and 12 thereby locking the head 59 to the stem 52. Optionally, each screw may be a self-tapping screw suitable for tapping into the plateau 54 of the stem 52, and each screw is inserted to a depth below a surface of the plateau 54 of the stem 52 to secure the head 59 to the stem 52.

The separate head 59, stem 52, and set screws 56a, 56b, 56c of the radial head replacement 50 according to the invention provide a radial head replacement system wherein the head portion of the implanted radial head replacement can be positioned in any number of spatial relationships relative to the stem and thereafter secured to the stem such that the head 59 smoothly interfaces with the capitellum 17 of the humerus 11 and the radial notch 25 of the ulna 15. The head 59 is adjustable in three planes: lateral-medial (a transverse direction in relation to the axis of the stem 52), posterior-anterior (another transverse direction in relation to the axis of the stem 52), and proximal-distal (an axial direction in relation to the axis of the stem 52) before being secured to the stem 52. As a result, the risk that the implanted radial head replacement may dislocate is minimized. Thus, the radial head replacement 50 overcomes the difficulties in getting the radial head replacement to track over the capitellum 17 of the humerus 11. Also, the separate head 59, stem 52, and set screws 56a, 56b, 56c of the radial head replacement 50 according to the invention may be provided in a kit of different sizes for use with the patients having different radius sizes.

Turning now to FIGS. 13-16, there is shown another embodiment of a radial head replacement 80 according to the invention. The radial head replacement 80 includes a head 89, a stem 82 and threaded bone screws 104, 106. The stem 82 is dimensioned to be received within the intramedullary canal of the radius 13. The head 89 of the radial head replacement 80 has a proximal concave surface 91 which is shaped for contact with the capitellum 17. The radius of curvature of the concave surface 91 is matched so as to approximate the radius of curvature of the capitellum 17. This concave surface 91 is surrounded by a peripheral rim 93, which lies at the proximal end of a peripheral surface 95 of the head 89. The head 89 has a medial region 97 and a lateral region 99. The surface of the medial region 97 of the periphery surface 95 of the head 89 articulates with the radial notch 25 in the side of the ulna 15. The head 89 has a channel 84 with internal threads 85 and a channel 86 with internal threads 87 that accept the bone screws 104, 106 respectively. Optionally, the threads 87 may be omitted, particularly when self-tapping screws are used. The elliptical design of the head 89 of the radial head replacement 80 better models the normal anatomy of the radial head.

The integral head 59 and stem 52, and the bone screws 104, 106 of the radial head replacement 80 are typically provided as separate components for assembly. However, the bone screws 104,106 may be provided in a partially inserted state in the head 89. The head 89, the bone screws 104, 106, and the stem 82 of the radial head replacement 80 may formed from a biocompatible material such as a titanium alloy (e.g., titanium-6-aluminum-4-vanadium), a cobalt alloy, a stainless steel alloy, a tantalum alloy, a nonresorbable ceramic such as aluminum oxide or zirconia, a nonresorbable polymeric material such as polyethylene, or a nonresorbable composite material such as a carbon fiber-reinforced polymer.

Figure 16:
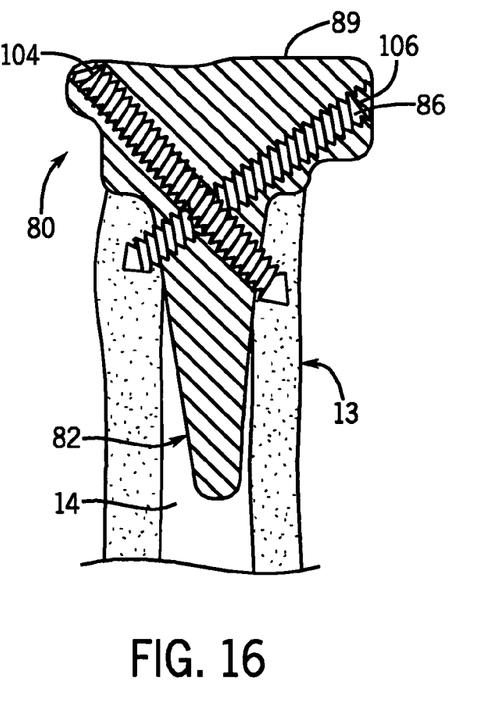
FIG. 16 is a cross sectional view of the radial head replacement of FIGS. 13-15 as implanted in the intramedullary canal of a radius.

The radial head replacement 80 may be implanted in the radius 13 as follows. First, the head of the radius 13 is resected and the intramedullary canal 14 of the radius 13 is inspected and tools (such as a reamer) may be used to clean material out of the intramedullary canal. Once the intramedullary canal in the radius 13 has been prepared, the surgeon can then insert the stem 82 (which is tapered for ease of insertion) into the intramedullary canal 14 of the radius 13. The bone screws 104, 106 are then screwed inwardly until the bone screws 104, 106 exit the channels 84, 86 respectively, and penetrate into the radius 13 as shown in FIG. 16. The crossed bone screws 104, 106 serve to more securely anchor the stem 82 of the radial head replacement 80 in the intramedullary canal 14 of the radius 13 without the need for cement.

Referring now to FIGS. 17-18 and 21-24, there is shown an apparatus 110 in accordance with the invention for guiding the resection of a radial head. Looking first at FIG. 17, there is a view of an elbow joint showing in cross section an intramedullary alignment shaft 112 of the apparatus 110 as implanted in the intramedullary canal 14 of a radius 13. The intramedullary alignment shaft 112 is cylindrical and has a concave bearing surface 114 at one end. The concave bearing surface 114 is shaped for contact with the capitellum 17. Preferably, the concave bearing surface 114 is shaped to conform to the proximal concave surface 61 of the head 59 of the radial head replacement 50 or to conform to the proximal concave surface 91 of the head 89 of the radial head replacement 80. The intramedullary alignment shaft 112 may be dimensioned for a snug fit in the intramedullary canal 14 of the radius 13, or may be dimensioned for clearance between the intramedullary alignment shaft 112 and the intramedullary canal 14 of the radius 13.

The apparatus 110 for guiding the resection of a radial head includes a cutting guide 140 as shown in FIGS. 21-24. The cutting guide 140 has a base comprising a vertical wall 146, and a top wall 142 that extends laterally from the vertical wall 146. The top wall 142 terminates in an outermost cutting guide edge 143. In the embodiment shown, the cutting guide edge 143 is parallel to the vertical wall 146. However, the cutting guide edge 143 may form an angle in relation to the vertical wall 146 to provide for an angled cut. The vertical wall 146 has a notch 148 in its lower portion that forms a pair of spaced apart legs 149a, 149b.

The apparatus 110 for guiding the resection of a radial head is used as follows. First, the head of the radius 13 is partially resected and the intramedullary canal 14 of the radius 13 is inspected and tools (such as a reamer) may be used to clean material out of the intramedullary canal. Once the intramedullary canal 14 in the radius 13 has been prepared, the surgeon can then insert the intramedullary alignment shaft 112 into the intramedullary canal 14 of the radius 13 into the position shown in FIG. 17. The intramedullary alignment shaft 112 is positioned such that the concave bearing surface 114 is in contact with the capitellum 17.

Figure 18:
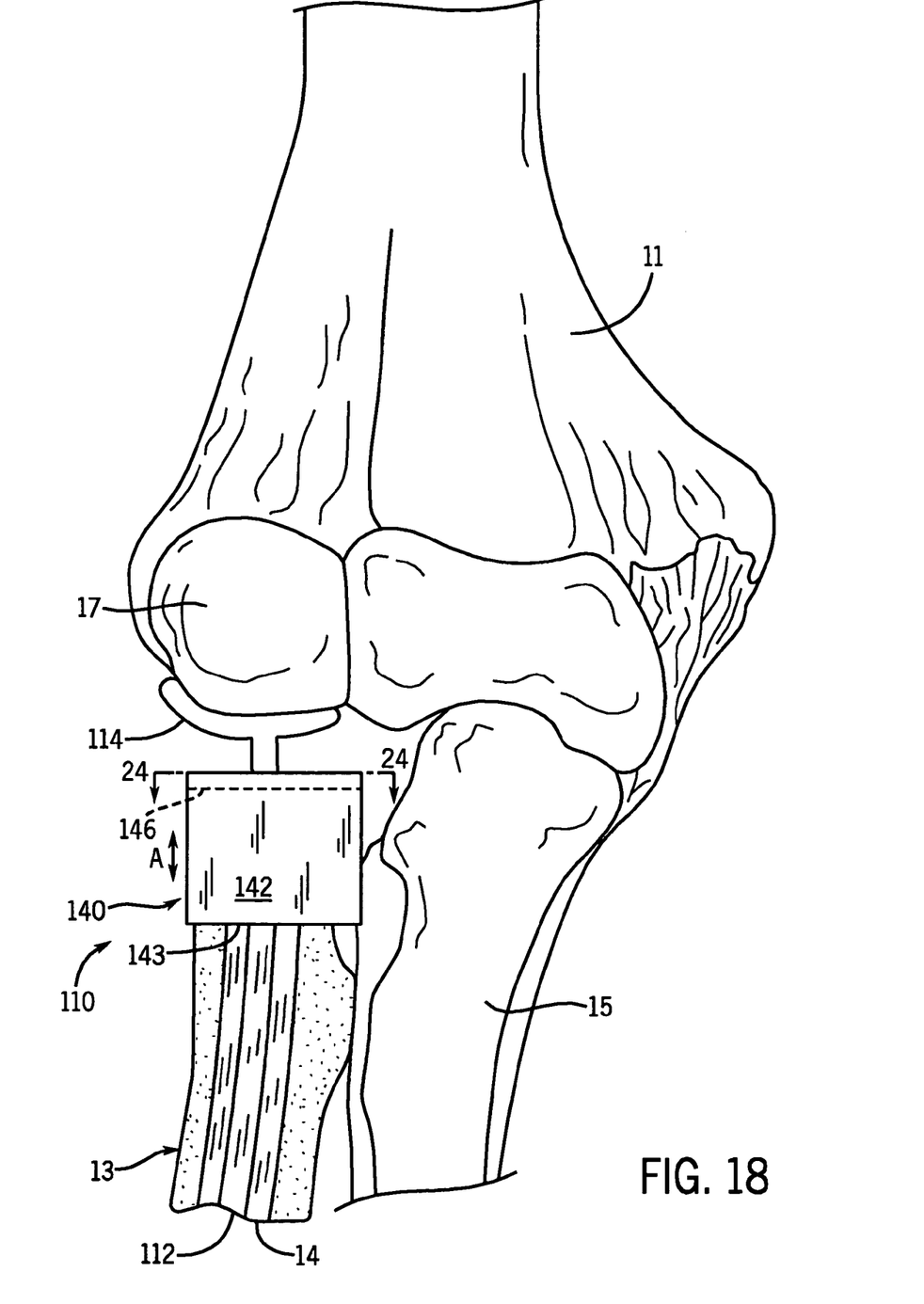
FIG. 18 is a top view of an elbow joint showing an apparatus for guiding the resection of a radial head as assembled before resection of a radius.
Figure 19:
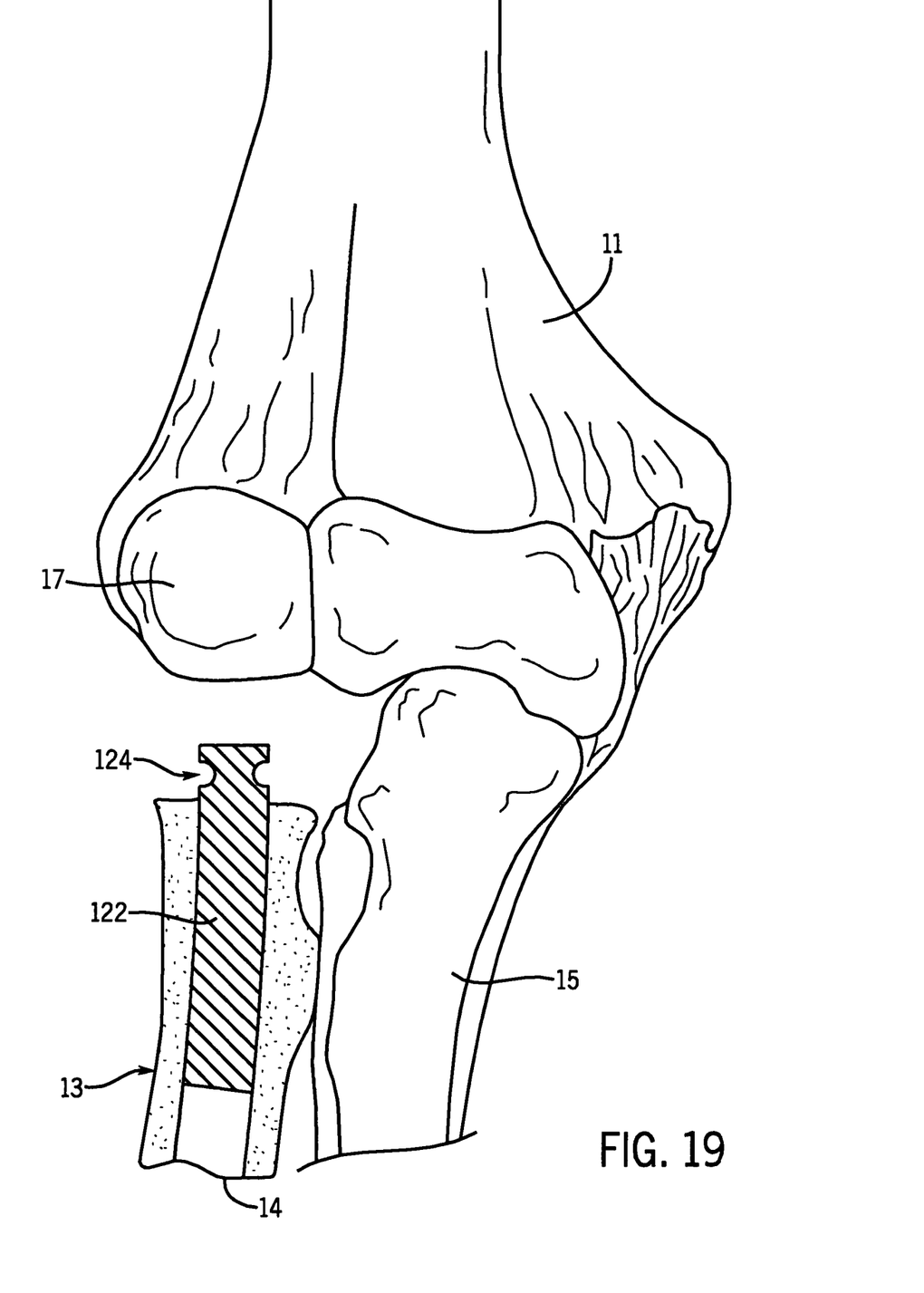
FIG. 19 is a top view of an elbow joint showing in cross section yet another embodiment of an intramedullary alignment shaft of an apparatus for guiding the resection of a radial head as implanted in the intramedullary canal of a radius.
Figure 24:
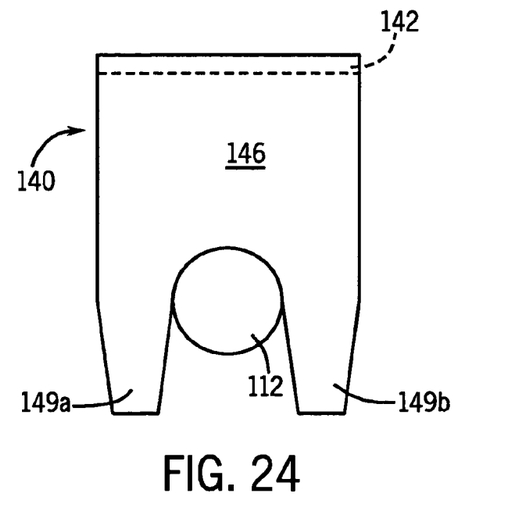
FIG. 24 is a view taken along line 24-24 of FIG. 18 with the radius removed for clarity.

Next, the cutting guide 140 is placed over the intramedullary alignment shaft 112 such that the notch 148 of the cutting guide 140 rests on the intramedullary alignment shaft 112 as shown in FIG. 24. In this arrangement, the cutting guide 140 may be moved in directions "A" as shown in FIG. 18 along the axis of the shaft 112. The surgeon may move the cutting guide to a desired location over the radius 13 and then the radius is resected accurately using a conventional surgical saw guided by the outermost cutting guide edge 143. As a result, the osteotomy cut of the natural radial head is made at an angle that corresponds to the angle between the stem and head portions of the radial head replacement. Thus, inaccurate resection and the associated dislocation risks noted above are avoided.

Figure 17:
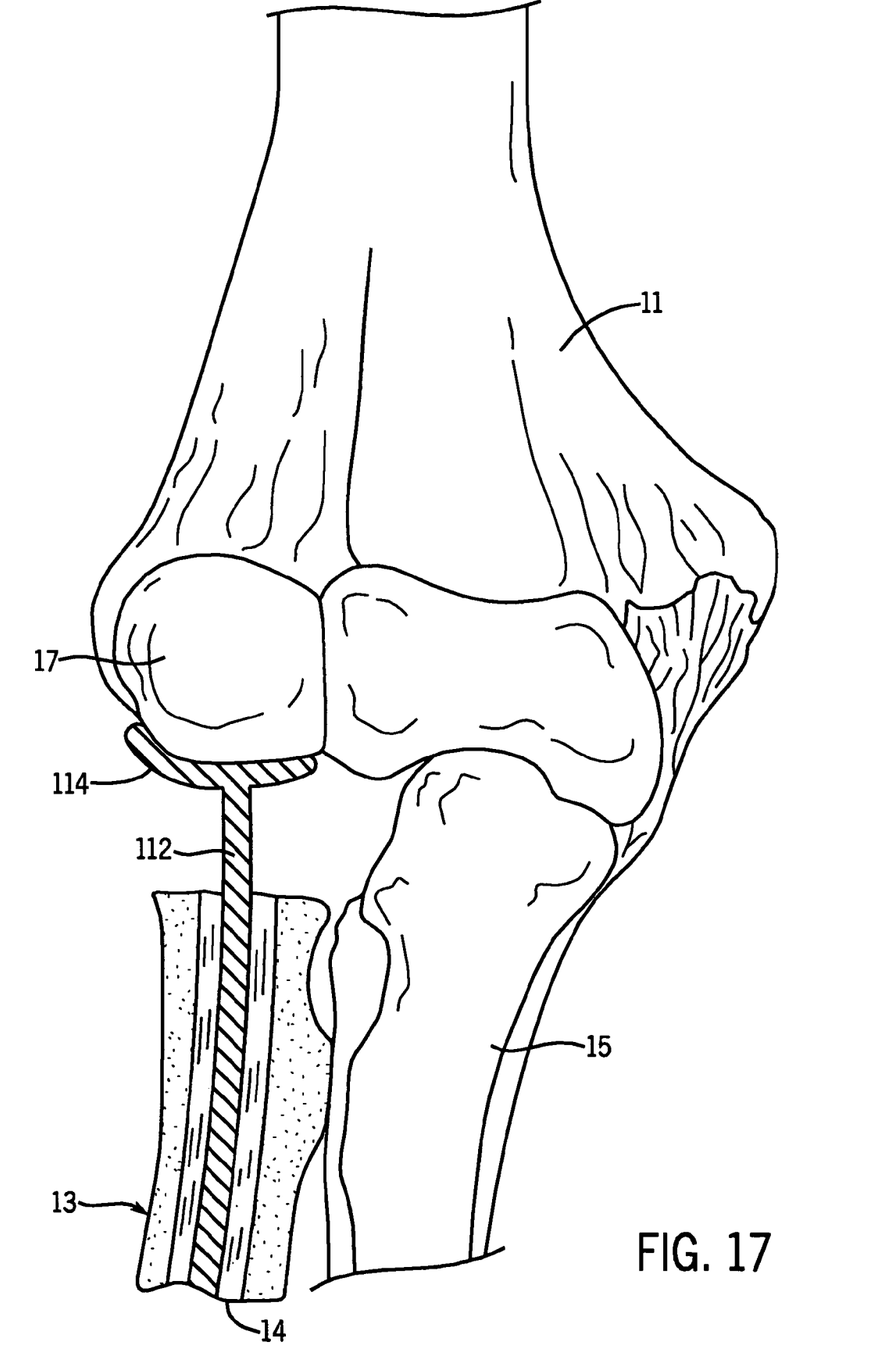
FIG. 17 is a top view of a human elbow joint showing in cross section an intramedullary alignment shaft of an apparatus for guiding the resection of a radial head as implanted in the intramedullary canal of a radius.
Figure 17A:
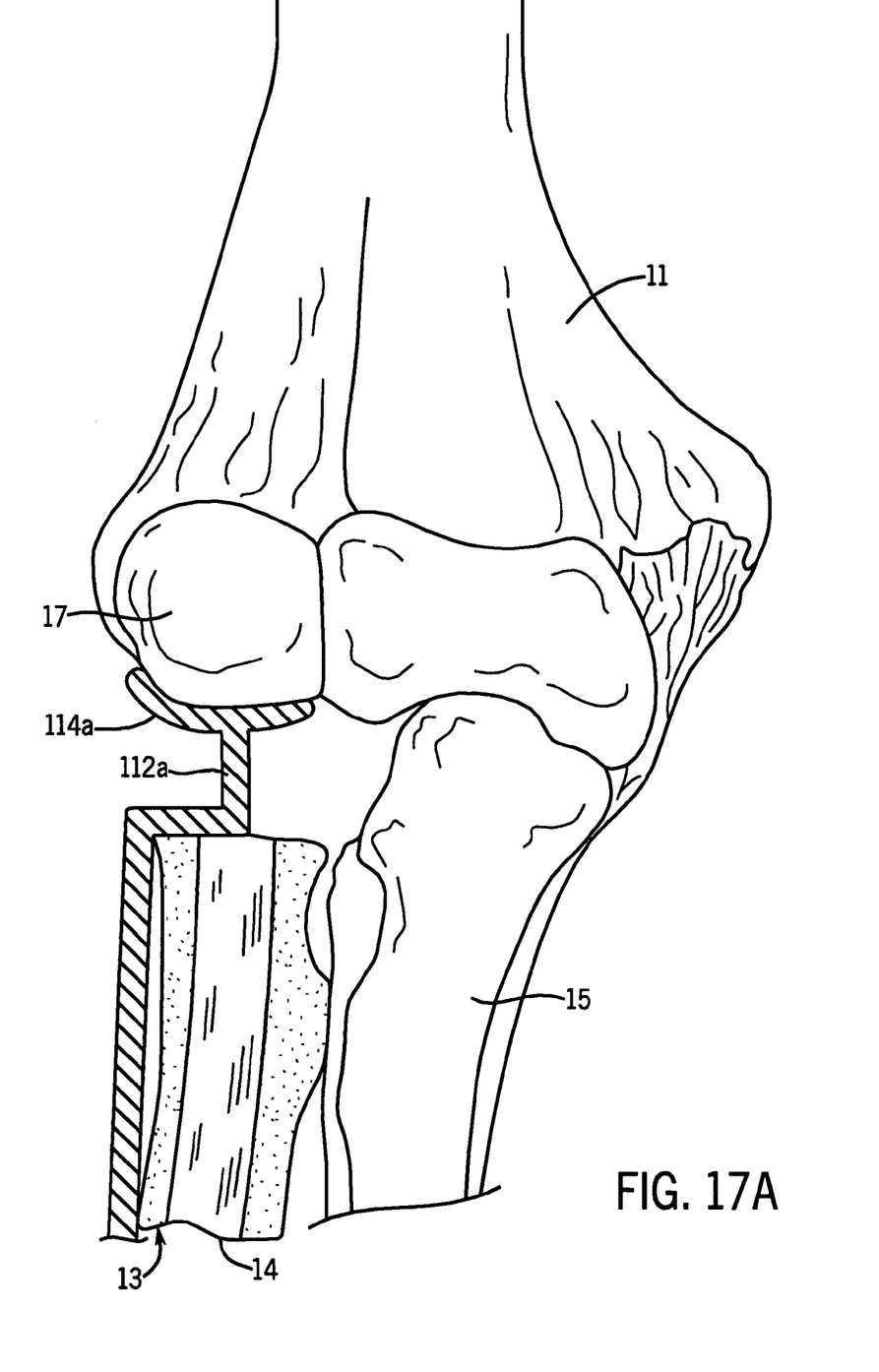
FIG. 17A is a top view of a human elbow joint showing in cross section an alignment shaft of another embodiment of an apparatus for guiding the resection of a radial head as implanted in the intramedullary canal of a radius.

Referring now to FIG. 17A, there is shown yet another apparatus in accordance with the invention for guiding the resection of a radial head. Looking at FIG. 17A, there is a horizontal top view of an elbow joint showing in cross section an alignment shaft 112a of the apparatus as positioned adjacent the outside of a radius 13. The alignment shaft 112a is cylindrical in cross-section and has a concave bearing surface 114a at one end. The concave bearing surface 114a is shaped for contact with the capitellum 17. Preferably, the concave bearing surface 114a is shaped to conform to the proximal concave surface 61 of the head 59 of the radial head replacement 50 or to conform to the proximal concave surface 91 of the head 89 of the radial head replacement 80.

In the alignment shaft 112a of the apparatus of FIG. 17A, the end portion of the alignment shaft 112a includes a cutting guide mounting section that is transversely offset from the alignment shaft 112a to allow the concave bearing surface 114a to contact the capitellum 17 while the alignment shaft 112a is placed along the outside of the radius 13. In particular, the apparatus of FIG. 17A is used as follows. First, the alignment shaft 112a is positioned such that the concave bearing surface 114a is in contact with the capitellum 17. The alignment shaft 112a is placed along the outside of the radius 13. The alignment shaft 112a is dimensioned to extend from the styloid process of the radius 13 to the end of the radius being resected, and the alignment shaft 112a may include a styloid marker at its end. Preferably, the cutting guide mounting section is dimensioned to be arranged along an axis of the intramedullary canal of the radius when in use.

Then, the cutting guide 140 is placed over the cutting guide mounting section of the alignment shaft 112a such that the notch 148 of the cutting guide 140 rests on the alignment shaft 112a as shown in FIG. 24. In this arrangement, the cutting guide 140 may be moved in directions parallel along the axis of the shaft 112a. The surgeon may move the cutting guide to a desired location over the radius 13 and then the radius is resected accurately using a conventional surgical saw guided by the outermost cutting guide edge 143. As a result, the osteotomy cut of the natural radial head is made at an angle that corresponds to the angle between the stem and head portions of the radial head replacement. Thus, inaccurate resection and the associated dislocation risks noted above are avoided.

Alternative arrangements of the end portion of the alignment shaft 112a are possible. For example, the end portion of the alignment shaft 112a may be shaped to conform to the radial notch 25 which is formed in the medial portion of the ulna 15. Various sizes of the end portion of the alignment shaft 112a may also be provided.

Figure 20:
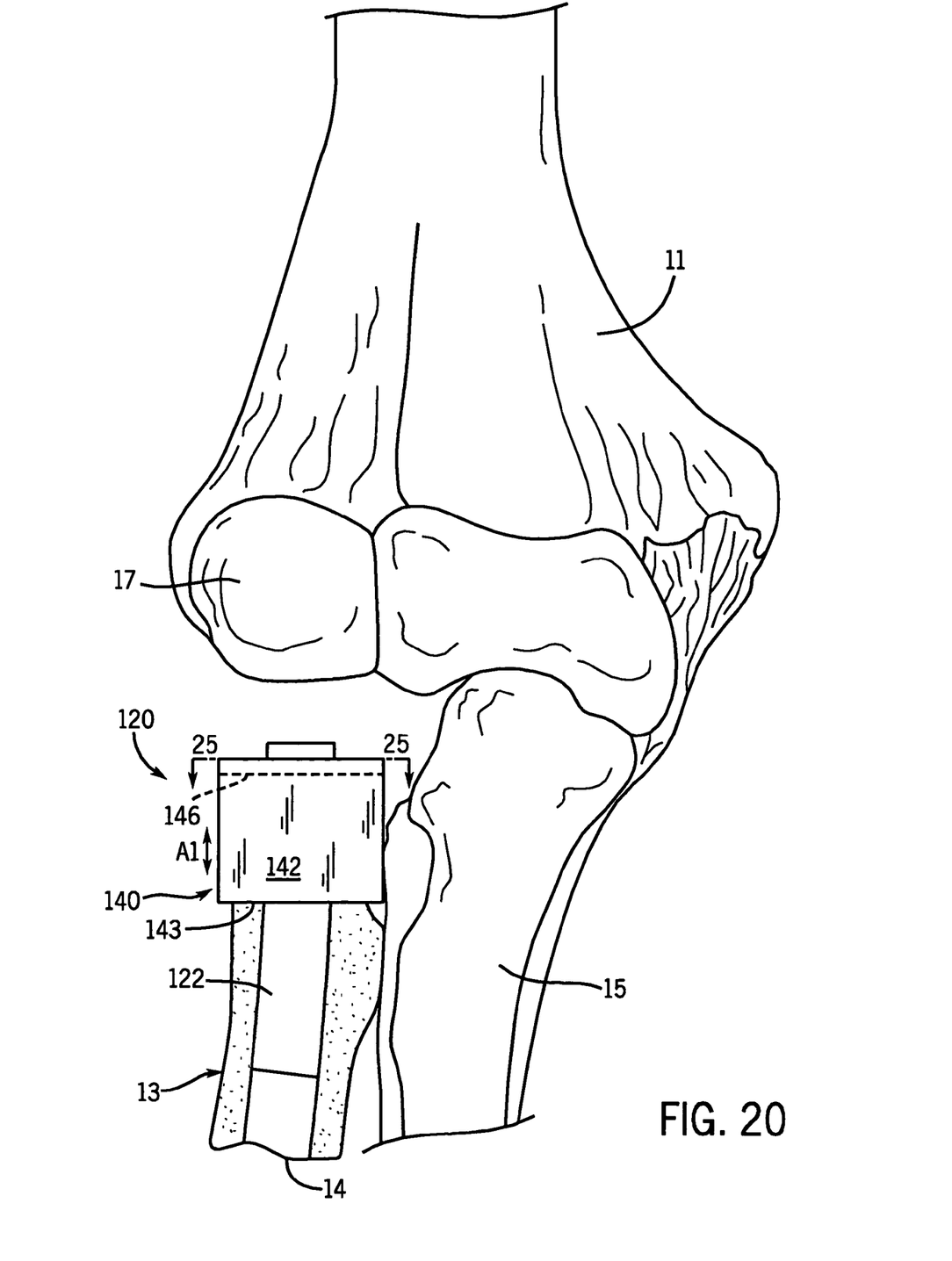
FIG. 20 is a top view of an elbow joint showing an apparatus for guiding the resection of a radial head as assembled before resection of a radius.
Figure 21:
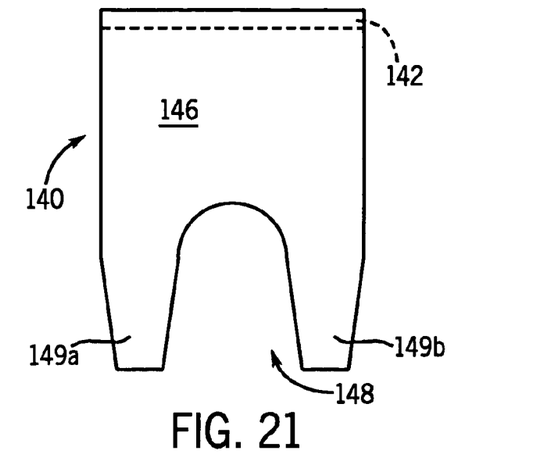
FIG. 21 is a front view of a cutting guide suitable for use with the intramedullary alignment shaft shown FIG. 17, FIG. 17A, or FIG. 19.
Figure 22:
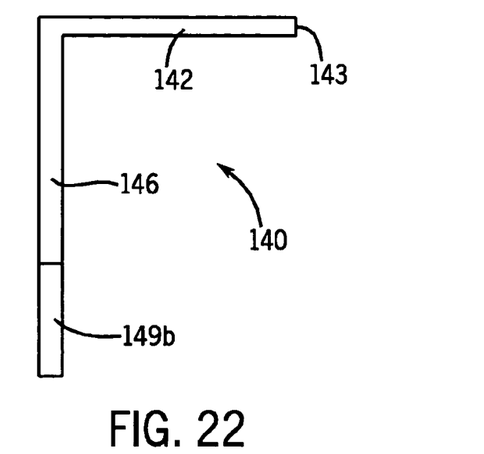
FIG. 22 is a side view of the cutting guide of FIG. 21.
Figure 23:
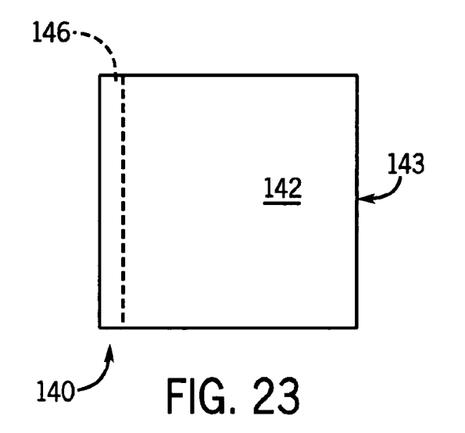
FIG. 23 is a top view of the cutting guide of FIG. 21.

Referring now to FIGS. 19-23 and 25, there is shown yet another apparatus 120 in accordance with the invention for guiding the resection of a radial head. Looking first at FIG. 19, there is a horizontal top view of an elbow joint showing in cross section an intramedullary alignment shaft 122 of the apparatus 120 as implanted in the intramedullary canal 14 of a radius 13. The intramedullary alignment shaft 122 is cylindrical and has a circumferential groove 124 spaced from one end. In the embodiment shown, the groove 124 is perpendicular to the axis of the shaft 122. However, the groove 124 could be angled in relation to the axis of the shaft 122 to provide an angled cut. The intramedullary alignment shaft 122 may be dimensioned for a snug fit in the intramedullary canal 14 of the radius 13, or may be dimensioned for clearance between the intramedullary alignment shaft 122 and the intramedullary canal 14 of the radius 13. The apparatus 120 for guiding the resection of a radial head includes the cutting guide 140 as shown in FIGS. 21-23 and described above.

The apparatus 120 for guiding the resection of a radial head is used as follows. First, the head of the radius 13 is partially resected and the intramedullary canal 14 of the radius 13 is inspected and tools (such as a reamer) may be used to clean material out of the intramedullary canal. Once the intramedullary canal 14 in the radius 13 has been prepared, the surgeon can then insert the intramedullary alignment shaft 122 into the intramedullary canal 14 of the radius 13 into the position shown in FIG. 19. The intramedullary alignment shaft 122 is positioned such that the circumferential groove 124 is spaced from the resected end of the radius.

Figure 25:
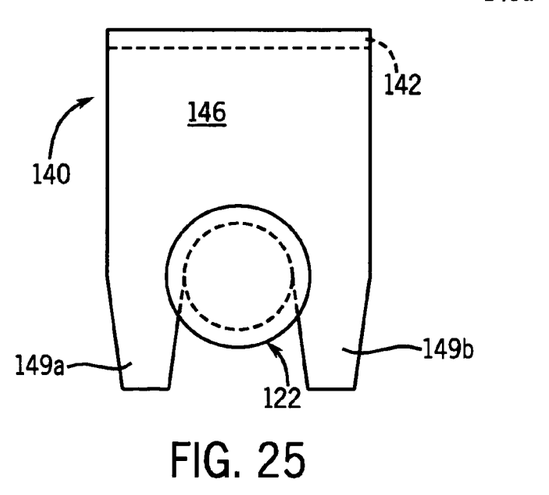
FIG. 25 is a view taken along line 25-25 of FIG. 20 with the radius removed for clarity.

Next, the cutting guide 140 is placed over the intramedullary alignment shaft 122 such that the notch 148 and at least part of the legs 149a, 149b of the cutting guide 140 rest in the groove 124 of the intramedullary alignment shaft 122 as shown in FIG. 25. In this arrangement, the cutting guide 140 is fixed against movement in directions "A1" as shown in FIG. 20. The radius is then resected accurately using a conventional surgical saw guided by the cutting guide edge 143. As a result, the osteotomy cut of the natural radial head is made at an angle that corresponds to the angle between the stem and head portions of the radial head replacement. Thus, inaccurate resection and the associated dislocation risks noted above are avoided. It is contemplated that the intramedullary alignment shaft 122 can also be configured to accept the head 59 of the radial head replacement 50 described above. In such a construction, the intramedullary alignment shaft 122 is left in the radius 13 after resection and the head 59 of the radial head replacement 50 is secured to the intramedullary alignment shaft 122 using set screws 56a, 56b, 56c in the manner described above.

Various sizes of the intramedullary alignment shaft 112, the alignment shaft 112a, the intramedullary alignment shaft 122, and the cutting guides 140 may be provided in a kit for use with the patients having different radius sizes and for use with different radial head replacements. For example, the length and width of the top wall 142 and the length and width of the vertical wall 146 of the cutting guide 140 may be varied. Also, the length and width of the intramedullary alignment shaft 112, the length and width of the alignment shaft 112a, and the length and width of the intramedullary alignment shaft 122 may be varied. In addition, the concave bearing surface 114 size may be varied.

Figures 26, 27:
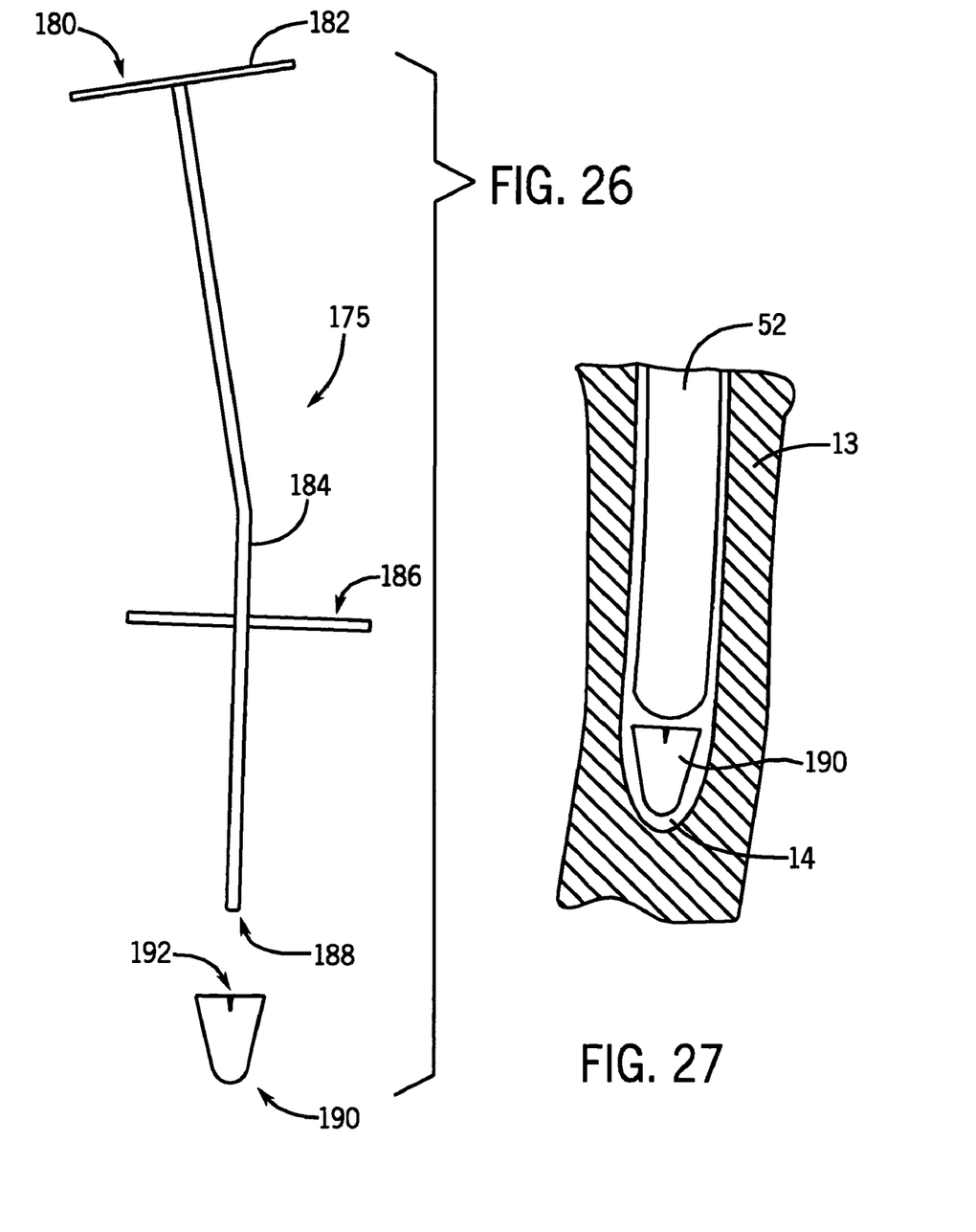
FIG. 26 is an exploded view of a bone plug and bone plug insertion instrument according to the invention.
FIG. 27 is a view showing the bone plug of FIG. 26 implanted in a radius (shown in cross-section) below the stem of a prosthesis.

Turning now to FIGS. 26-27, there is shown an apparatus for plugging an open end of an intramedullary canal of the radius to restrict the flow of a cement used to fix a prosthesis stem inserted into the open end of the canal. The apparatus 175 includes a bone plug 190 formed from a medical grade material such as a nonresorbable polymeric material (e.g., polyethylene). The plug 190 is dimensioned to seal the intramedullary canal 14 at a location below an end of the prosthesis stem 52 and prevent the flow of cement beyond the location. The plug 190 has a mounting hole 192 in its upper surface.

The apparatus 175 also includes an insertion instrument 180 for placing the plug 190 in the canal 14 of the radius 13. The lower portion of the insertion instrument 180 is dimensioned to fit in the canal 14 of the radius 15. The insertion instrument 180 has a handle 182 for manipulating the instrument 180, and has a lower end 188 dimensioned to engage the mounting hole 192 when placing the plug 190 in the canal 14. The insertion instrument 180 also has a lateral crosspiece 186 to facilitate placement of the plug 190 at a predetermined depth in the canal 14. The crosspiece 186 is used to gauge the distance from the plug 190 to the top end of the radius 13. The lateral crosspiece 186 may be movable on the shaft 184 of the insertion instrument 180. Once plug 190 is pushed into the intramedullary canal 14, the insertion instrument is removed from the mounting hole 192 and the canal 14, and acrylic cement is forced into the open end of the canal 14. The plug 190 provides an effective seal within the intramedullary canal 14 of the radius 13, and prevents the cement from traveling beyond the desired point of fixation.

Therefore, it can be seen that the invention provides a total radial head replacement system. The total radial head replacement system may include either radial head replacement 50 or radial head replacement 80, apparatus 110 or apparatus 120 for guiding the resection of a radial head, and the bone plug 160 and insertion instrument 170.

While the invention has been described with reference to the replacement of a radial head, the methods and devices of the invention may be used to replace the end portion of other bones such as, for example, the tibia and the femur. Thus, the invention is not limited to radial head replacement. Therefore, one skilled in the art will appreciate that the present invention can be practiced by other than the described embodiments, which have been presented for purposes of illustration and not of limitation. Accordingly, the scope of the appended claims should not be limited to the description of the embodiments contained herein.

What is claimed is:

1. A modular prosthesis for replacing an end portion of a bone, the prosthesis comprising:
    a stem dimensioned to be received in the intramedullary canal of the bone;
    a head having an outer wall defining an interior space dimensioned such that the head can be placed over an end portion of the stem, the outer wall having an opening, the outer wall being dimensioned such that the head can be translated in an axial direction in relation to an axis of the stem and the head can be translated in a transverse direction in relation to the axis of the stem when the end portion of the stem is placed in the interior space of the head, the outer wall of the head of the prosthesis including a concave surface dimensioned to interface with another bone when the head of the prosthesis is secured to the stem; and
    a screw dimensioned to be arranged in the opening,
    wherein the screw is suitable for contacting the end portion of the stem when arranged in its associated opening to secure the head to the stem by constraining movement of the head in the axial direction and in the transverse direction, and
    wherein the opening is in a lateral direction in relation to the axis of the stem, and
    wherein an interior surface of the outer wall of the head adjacent the opening is spaced from the end portion of the stem when the head is secured to the stem, and
    wherein the end portion of the stem includes an end surface and a side surface extending away from the end surface, the side surface having a curved periphery when viewed in a cross-section transverse to the axis of the stem, and
    wherein the screw contacts the side surface of the end portion of the stem when the head is secured to the stem.

2. The prosthesis of claim 1 wherein:
    the screw is a self-tapping screw suitable for tapping into the end portion of the stem, and
    the screw is inserted to a depth below a surface of the end portion of the stem to secure the head to the stem.

3. The prosthesis of claim 1 wherein:
    the outer wall of the head has three openings, and two of the three openings are on opposed sides of the outer wall.

4. The prosthesis of claim 1 wherein:
    the outer wall is dimensioned such that the head can be moved in a second transverse direction in relation to the axis of the stem at an angle to the transverse direction when the head is placed over the end portion of the stem, and
    the screw is suitable for contacting the end portion of the stem when arranged in its associated opening to constrain movement of the head in the second transverse direction.

5. The prosthesis of claim 1 wherein:
    the prosthesis is adapted to replace a radial head.

6. The prosthesis of claim 5 wherein:
    the head of the prosthesis is elliptical, and
    the concave surface of the head is dimensioned to interface with the capitellum of the humerus and the outer wall of the head of the prosthesis includes a periphery surface dimensioned to interface with the radial notch of the ulna when the head of the prosthesis is secured to the stem.

7. A modular prosthesis for replacing an end portion of a bone, the prosthesis comprising:
    a stem dimensioned to be received in the intramedullary canal of the bone;
    a head having an outer wall defining an interior space dimensioned such that the head can be placed over an end portion of the stem, the outer wall having an opening, the outer wall being dimensioned such that the head can be translated in a first transverse direction in relation to an axis of the stem and the head can be translated in a second transverse direction in relation to the axis of the stem at an angle to the first transverse direction when the end portion of the stem is placed in the interior space of the head, the outer wall of the head of the prosthesis including a concave surface dimensioned to interface with another bone when the head of the prosthesis is secured to the stem; and
    a screw dimensioned to be arranged in the opening,
    wherein the screw is suitable for contacting the end portion of the stem when arranged in its associated opening to secure the head to the stem by constraining movement of the head in the first transverse direction and in the second transverse direction, and
    wherein the opening is in a lateral direction in relation to the axis of the stem, and
    wherein an interior surface of the outer wall of the head adjacent the opening is spaced from the end portion of the stem when the head is secured to the stem, and
    wherein the end portion of the stem includes a top end surface and a side surface extending away from the end surface, the side surface having a curved periphery when viewed in a cross-section transverse to the axis of the stem, and
    wherein the screw contacts the side surface of the end portion of the stem when the head is secured to the stem.

8. The prosthesis of claim 7 wherein:
    the prosthesis is adapted to replace a radial head.

9. The prosthesis of claim 8 wherein:
    the head of the prosthesis is elliptical, and
    the concave surface of the head is dimensioned to interface with the capitellum of the humerus and the outer wall of the head of the prosthesis includes a periphery surface dimensioned to interface with the radial notch of the ulna when the head of the prosthesis is secured to the stem.

10. A modular prosthesis for replacing an end portion of a bone, the prosthesis comprising:
a stem dimensioned to be received in the intramedullary canal of the bone;
a head having an outer wall defining an interior space dimensioned such that the head can be placed over an end portion of the stem, the outer wall having an opening, the outer wall being dimensioned such that the head can be moved in an axial direction in relation to an axis of the stem and the head can be moved in a transverse direction in relation to the axis of the stem when the head is placed over the end portion of the stem; and
a screw dimensioned to be arranged in the opening,
wherein the screw is suitable for contacting the end portion of the stem when arranged in its associated opening to secure the head to the stem by constraining movement of the head in the axial direction and in the transverse direction, and
wherein the opening is in a lateral direction in relation to the axis of the stem, and
wherein an interior surface of the outer wall of the head adjacent the opening is spaced from the end portion of the stem when the head is secured to the stem, and
wherein the end portion of the stem includes a top end surface and a side surface extending away from the end surface, the side surface having a curved periphery when viewed in a cross-section transverse to the axis of the stem, and
wherein the screw contacts the side surface of the end portion of the stem when the head is secured to the stem, and
wherein the prosthesis is adapted to replace a radial head, and
wherein the head of the prosthesis is elliptical, and
wherein the outer wall of the head of the prosthesis includes a concave surface dimensioned to interface with the capitellum of the humerus and a periphery surface dimensioned to interface with the radial notch of the ulna when the head of the prosthesis is secured to the stem.

11. The prosthesis of claim 10 wherein:
the screw is a self-tapping screw suitable for tapping into the end portion of the stem, and
the screw is inserted to a depth below a surface of the end portion of the stem to secure the head to the stem.

12. The prosthesis of claim 10 wherein:
the outer wall of the head has three openings, and two of the openings are on opposed sides of the outer wall.

13. The prosthesis of claim 10 wherein:
the outer wall is dimensioned such that the head can be moved in a second transverse direction in relation to the axis of the stem at an angle to the transverse direction when the head is placed over the end portion of the stem, and
the screw is suitable for contacting the end portion of the stem when arranged in its associated opening to constrain movement of the head in the second transverse direction.

14. A modular prosthesis for replacing an end portion of a bone, the prosthesis comprising:
a stem dimensioned to be received in the intramedullary canal of the bone;
a head having an outer wall defining an interior space dimensioned such that the head can be placed over an end portion of the stem, the outer wall having an opening, the outer wall being dimensioned such that the head can be moved in a first transverse direction in relation to an axis of the stem and the head can be moved in a second transverse direction in relation to the axis of the stem at an angle to the first transverse direction when the head is placed over the end portion of the stem; and
a screw dimensioned to be arranged in the opening,
wherein the screw is suitable for contacting the end portion of the stem when arranged in its associated opening to secure the head to the stem by constraining movement of the head in the first transverse direction and in the second transverse direction, and
wherein the opening is in a lateral direction in relation to the axis of the stem, and
wherein an interior surface of the outer wall of the head adjacent the opening is spaced from the end portion of the stem when the head is secured to the stem, and
wherein the end portion of the stem includes an end surface and a side surface extending away from the end surface, the side surface having a curved periphery when viewed in a cross-section transverse to the axis of the stem , and
wherein the screw contacts the side surface of the end portion of the stem when the head is secured to the stem, and
wherein the prosthesis is adapted to replace a radial head, and
wherein the head of the prosthesis is elliptical, and
the outer wall of the head of the prosthesis includes a concave surface dimensioned to interface with the capitellum of the humerus and a periphery surface dimensioned to interface with the radial notch of the ulna when the head of the prosthesis is secured to the stem.

15. The prosthesis of claim 14 wherein:
the screw is a self-tapping screw suitable for tapping into the end portion of the stem, and
the screw is inserted to a depth below a surface of the end portion of the stem to secure the head to the stem.

16. The prosthesis of claim 14 wherein:
the outer wall of the head has three openings, and two of the three openings are on opposed sides of the outer wall.

* * * * *